US012770366B2

(12) United States Patent
Jeong

(10) Patent No.: US 12,770,366 B2
(45) Date of Patent: Oct. 20, 2026

(54) DATA PROCESSING METHOD, COMPUTER PROGRAM AND DEVICE

(71) Applicant: AIRS MEDICAL INC., Seoul (KR)

(72) Inventor: Keunwoo Jeong, Seoul (KR)

(73) Assignee: AIRS MEDICAL INC., Seoul (KR)

( * ) Notice: Subject to any disclaimer, the term of this patent is extended or adjusted under 35 U.S.C. 154(b) by 195 days.

(21) Appl. No.: 18/721,784

(22) PCT Filed: Jun. 21, 2023

(86) PCT No.: PCT/KR2023/008628

§ 371 (c)(1),
(2) Date: Jun. 19, 2024

(87) PCT Pub. No.: WO2023/249411

PCT Pub. Date: Dec. 28, 2023

(65) Prior Publication Data

US 2025/0054213 A1 Feb. 13, 2025

(30) Foreign Application Priority Data

Jun. 22, 2022 (KR) ........................ 10-2022-0075949

(51) Int. Cl.

| | |
|---|---|
| ***G16H 30/20*** | (2018.01) |
| ***G06T 11/00*** | (2026.01) |
| ***G06T 11/60*** | (2006.01) |
| ***G06V 10/762*** | (2022.01) |
| ***G06V 10/774*** | (2022.01) |

(52) U.S. Cl.

CPC ............ *G06V 10/762* (2022.01); *G06T 11/00* (2013.01); *G06T 11/60* (2013.01); *G06V 10/774* (2022.01); *G16H 30/20* (2018.01)

(58) Field of Classification Search

CPC ................................ G16H 30/20; G06T 11/00

See application file for complete search history.

(56) References Cited

U.S. PATENT DOCUMENTS

| | | | | |
|---|---|---|---|---|
| 2021/0290191 | A1* | 9/2021 | Qi | A61B 6/032 |
| 2021/0311151 | A1* | 10/2021 | Francavilla | G01R 33/5608 |

FOREIGN PATENT DOCUMENTS

| | | | |
|---|---|---|---|
| KR | 10-2003-0071833 A | 9/2003 |
| KR | 10-2003-0095298 A | 12/2003 |
| KR | 10-2015-0021904 A | 3/2015 |
| KR | 10-2015-0047109 A | 5/2015 |

(Continued)

OTHER PUBLICATIONS

Supplementary European Search Report for U.S. Appl. No. 23/827,521, dated Aug. 28, 2025, 1 pg., European Patent Office, Germany.

(Continued)

*Primary Examiner* — Matthew Salvucci
(74) *Attorney, Agent, or Firm* — McDonald Hopkins LLC

(57) ABSTRACT

A data processing method that is performed by a computing device including at least one processor according to an embodiment of the present disclosure includes: grouping a plurality of coil images, generated based on signals received from a plurality of coils, into a plurality of groups; and, for each of the plurality of groups, generating a group image by combining coil images included in each group; and a plurality of group images are noise-independent of each other.

14 Claims, 6 Drawing Sheets

(56) References Cited

FOREIGN PATENT DOCUMENTS

| | | | |
|---|---|---|---|
| KR | 10-1967242 | B1 | 4/2019 |
| KR | 10-2019-0131031 | A | 11/2019 |

OTHER PUBLICATIONS

Juhyung Park et al., "Coil to Coil: Self-supervised denoising using phased-array coil images", Proceedings of The International Society For Magnetic Resonance In Medicine, 30th Annual Meeting and Exhibition, vol. 30, 1157, 2022, XP040727705.

Jure Zbontar et al., "fastMRI: An Open Dataset and Benchmarks for Accelerated MRI", Arxiv.Org XP081557510, Cornell University Library, 201 Olin Library Cornell University Ithaca, NY, Nov. 21, 2018.

International Search Report for corresponding International Application No. PCT/KR2023/008628 mailed Oct. 4, 2023.

Written Opinion for corresponding International Application No. PCT/KR2023/008628 dated Oct. 4, 2023.

* cited by examiner

[FIG. 1]
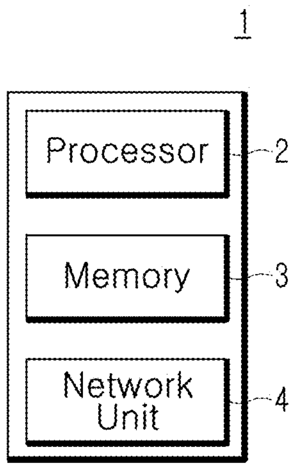
[FIG. 2]
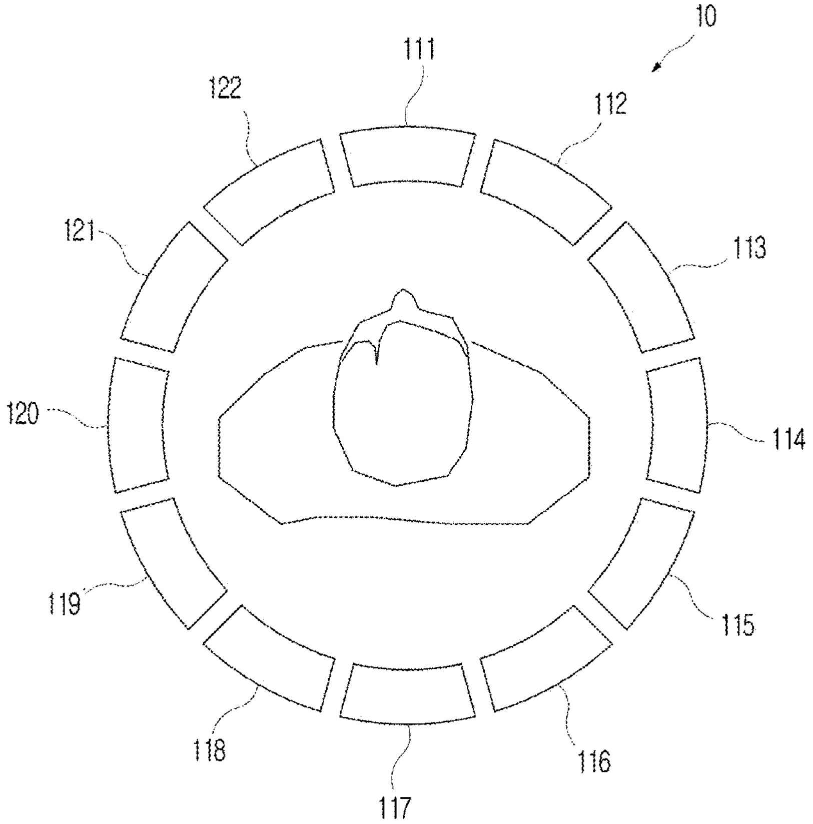

[FIG. 3]
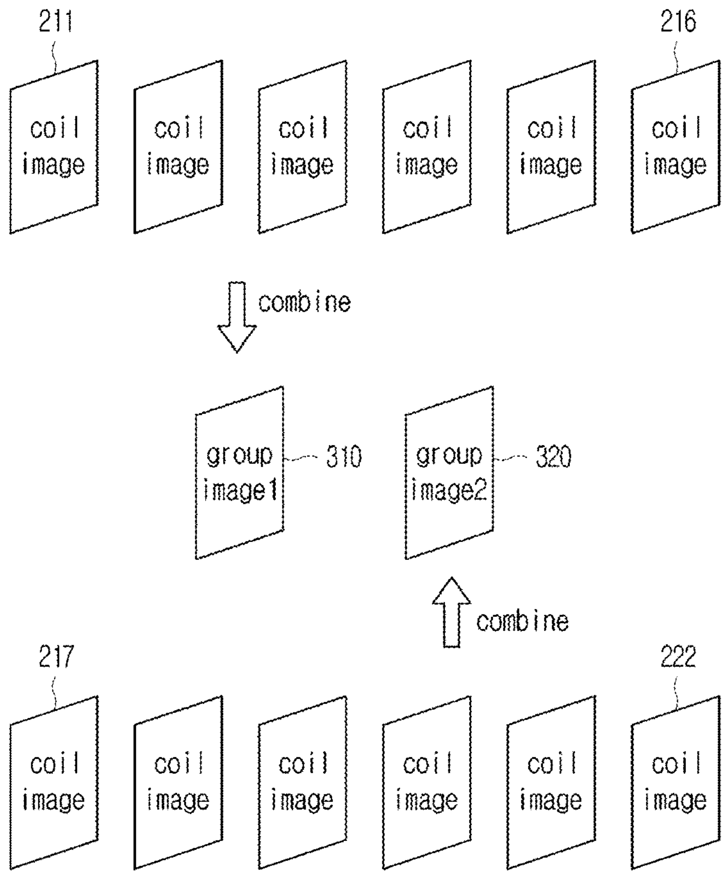

[FIG. 4]
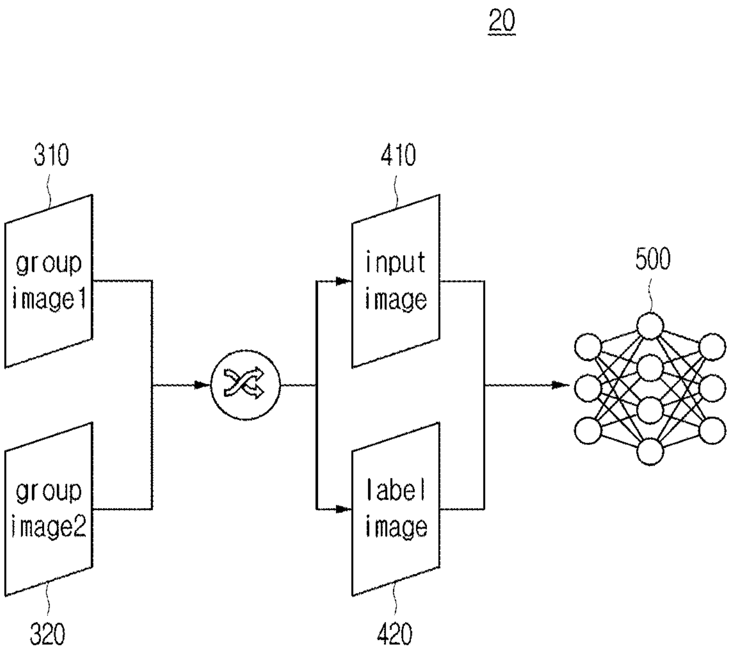
[FIG. 5]
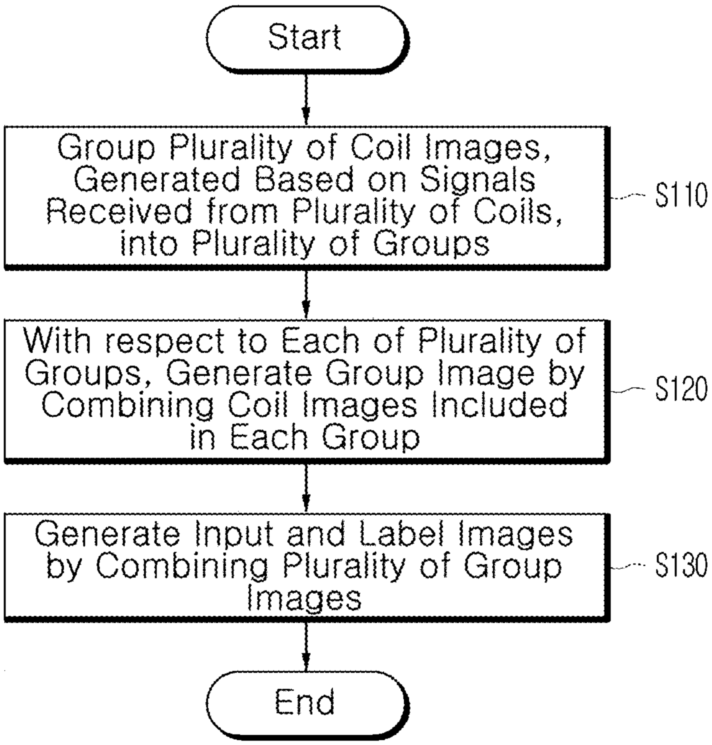

[FIG. 6]
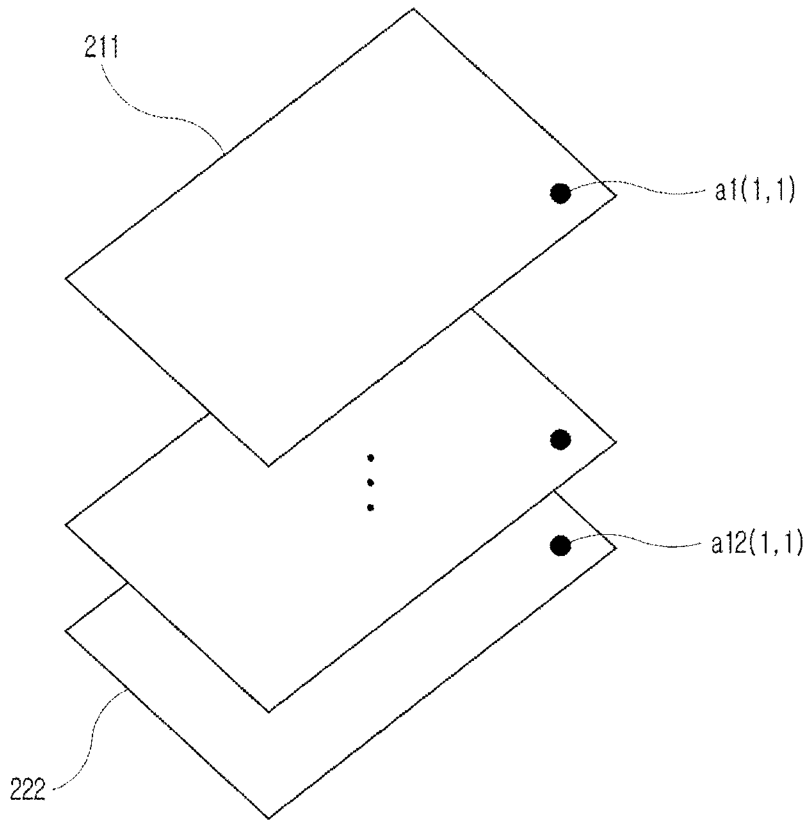

[FIG. 7]
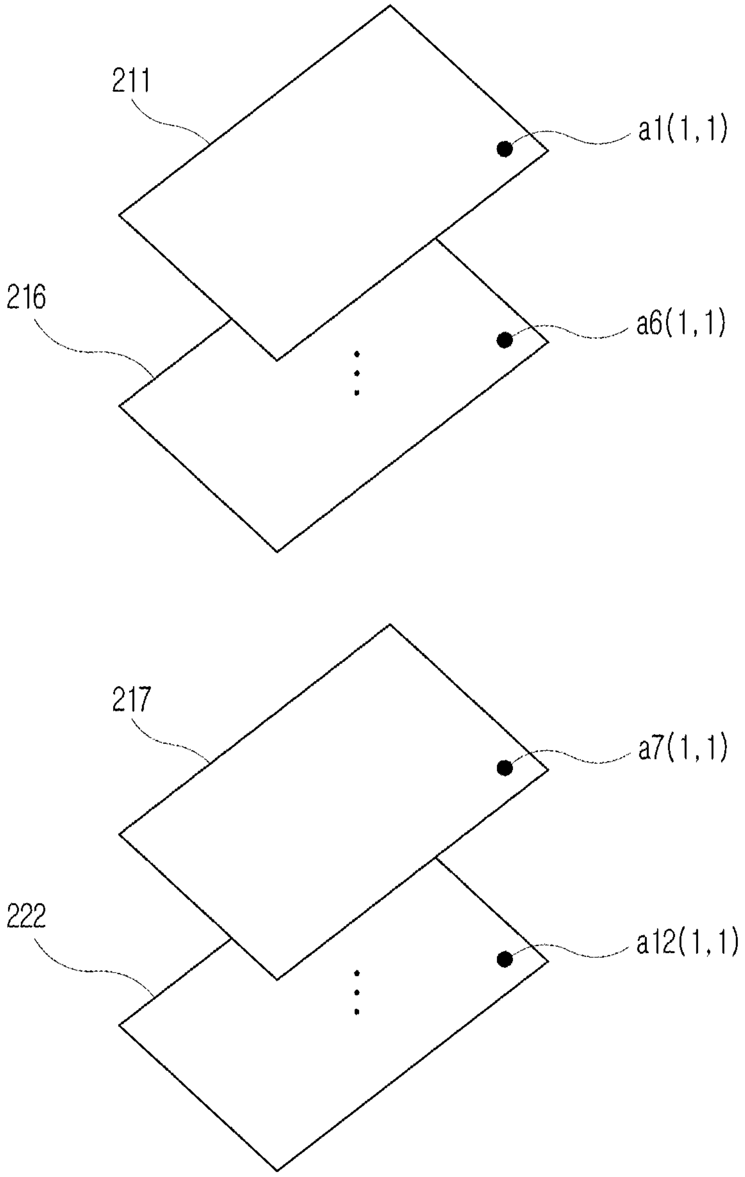

[FIG. 8]
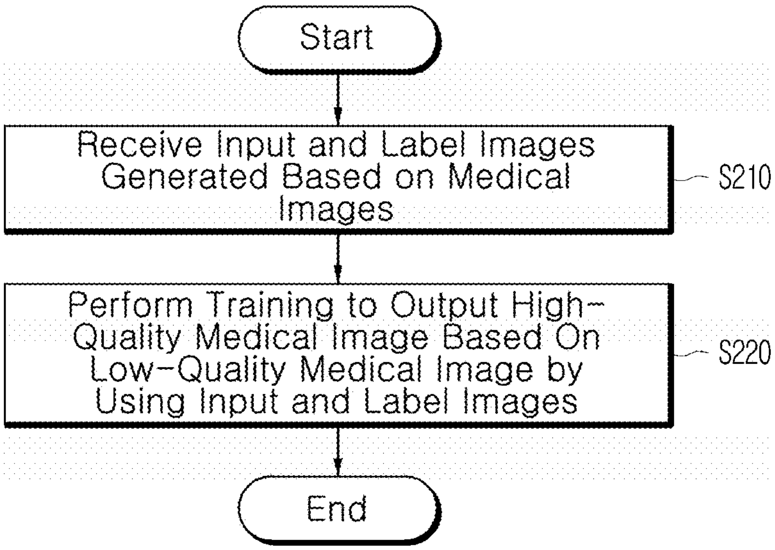

DATA PROCESSING METHOD, COMPUTER PROGRAM AND DEVICE

TECHNICAL FIELD

The present disclosure relates to a data processing method, computer program and device, and more particularly to a method, computer program and device for processing data using medical images.

BACKGROUND ART

In general, a medical imaging apparatus is an apparatus that acquires a patient's body information and provides images. Such medical imaging apparatuses include X-ray imaging apparatuses, ultrasound diagnostic apparatuses, computed tomography apparatuses, and magnetic resonance imaging (MRI) apparatuses.

A magnetic resonance imaging (MRI) apparatus requires a considerable amount of time for imaging. Therefore, in the medical industry, acceleration imaging techniques to shorten MRI acquisition times are of significant importance. For accelerated MRI images to be usable in medical settings, they must include all necessary information about the subject while minimizing noise that could affect interpretation. Recently, due to this need, techniques have been developed to restore low-quality accelerated MRI images to high-quality states using artificial intelligence (AI).

To restore accelerated MRI images to high quality using AI, it is essential to effectively train the AI model. This requires not only high-quality input data but also corresponding high-quality label data. However, even if a certain level of accelerated MRI input data is obtained, there is a practical issue in that corresponding high-quality restored images are almost nonexistent. Therefore, securing the necessary training data is fundamental for building an AI model.

Meanwhile, according to the noise-to-noise principle, an artificial neural network that performs noise reduction may be trained by using image pairs having the same signal strength and independent noise patterns as training data. For example, in the case of magnetic resonance images, in order to obtain images having the same signal strength and independent noise patterns, the same imaging needs to be performed twice, so that there is the inconvenience of taking twice as much time.

DISCLOSURE

Technical Problem

The present disclosure is intended to overcome the problems of the prior art described above, and is directed to a data processing method, computer program and device that generate training data by using coil images obtained from a multi-channel coil system.

However, objects to be achieved by the embodiments are not limited to the above-described object, and other objects may be present.

Technical Solution

According to an embodiment of the present disclosure for achieving the above-described object, there is disclosed a data processing method performed by a computing device. The data processing method includes: grouping a plurality of coil images, generated based on signals received from a plurality of coils, into a plurality of groups; and, for each of the plurality of groups, generating a group image by combining coil images included in each group; and a plurality of group images are noise-independent of each other.

Alternatively, the plurality of groups may include a first group and a second group, and grouping the plurality of coil images into the plurality of groups may include grouping the plurality of coil images so that the sensitivity characteristics of the first group images of the first group correspond to the sensitivity characteristics of the second group images of the second group.

Alternatively, grouping the plurality of coil images into the plurality of groups may include grouping the plurality of coil images so that the standard deviation of a sensitivity map corresponding to the first group images and the standard deviation of the sensitivity map corresponding to the second group images are each minimized.

Alternatively, grouping the plurality of coil images into the plurality of groups may include grouping the plurality of coil images so that the difference between a sensitivity map corresponding to the first group images and a sensitivity map corresponding to the second group images is minimized.

Alternatively, generating the group image by combining the coil images included in each group may include combining the coil images included in each group SO that the sensitivity characteristics of individual group images correspond to each other.

Alternatively, generating the group image by combining the coil images included in each group may include generating the group image by adaptively combining the coil images included in each group by using a sensitivity adjustment coefficient determined based on the sensitivity of coils corresponding to each group.

Alternatively, the plurality of groups may include a first group and a second group, and generating the group image by combining the coil images included in each group may include generating a first group image of the first group and a second group image of the second group based on a first sensitivity adjustment coefficient determined to be applied to the pixels of first locations for the coil images of the first group and a second sensitivity adjustment coefficient determined to be applied to the pixels of first locations for the coil images of the second group.

Alternatively, with respect to the pixels of the first locations, when sensitivity of coils corresponding to the first group is higher than sensitivity of coils corresponding to the second group, the first sensitivity adjustment coefficient is smaller than the second sensitivity adjustment coefficient.

Alternatively, the plurality of coil images may be generated based on the signals obtained by imaging an object once.

Alternatively, the plurality of coil images may be generated based on the signals obtained by performing accelerated imaging on the object.

Alternatively, the data processing method may further include generating input and label images to be input to an artificial neural network model that outputs high-quality medical image based on a low-quality medical image by combining the plurality of group images.

According to an embodiment of the present disclosure for achieving the above-described object, there is disclosed a data processing device. The data processing device includes: memory configured to store a plurality of coil images generated based on the signals received from a plurality of coils; and a processor configured to group the plurality of coil images into a plurality of groups and, for each of the plurality of groups, generate a group image by combining coil images included in each group; and the plurality of group images are noise-independent of each other.

Alternatively, the processor may combine the coil images included in each group based on the sensitivity characteristics of coils corresponding to each group and a sensitivity adjustment coefficient reflecting the pixel locations of each coil image therein.

Alternatively, the processor may group the plurality of coil images into a first group and a second group, and, with respect to the pixels of first locations for the individual coil images, when the sensitivity of coils corresponding to the first group is higher than the sensitivity of coils corresponding to the second group, combine the coil images by applying a sensitivity adjustment coefficient smaller than the sensitivity adjustment coefficient of the coil images of the second group to the coil images of the first group.

According to an embodiment of the present disclosure for achieving the above-described object, there is disclosed a computer program stored in a computer-readable storage medium. The computer program performs operations of generating training data when executed on at least one processor. The operations include operations of: grouping a plurality of coil images, generated based on the signals received from a plurality of coils, into a plurality of groups; and, for each of the plurality of groups, generating a group image by combining coil images included in each group, and a plurality of group images are noise-independent of each other.

Advantageous Effects

According to the solution of the present disclosure described above, the present disclosure may generate high-quality learning data having uniform image characteristics by using medical images acquired through a single imaging in a multi-channel coil system, so that the time and cost required for preparing training data for an artificial neural network model can be reduced.

DESCRIPTION OF DRAWINGS

FIG. 1 is a block diagram of a computing device according to an embodiment of the present disclosure;

FIG. 2 is an exemplary diagram showing the arrangement of coils of a multi-channel coil system according to an embodiment of the present disclosure;

FIGS. 3 and 4 are diagrams illustrating a method of operating a data processing device according to an embodiment of the present disclosure;

FIG. 5 is a flowchart showing a method of operating a data processing device according to an embodiment of the present disclosure;

FIGS. 6 and 7 are diagrams illustrating the combination operation of a data processing device according to an embodiment of the present disclosure; and FIG. 8 is a flowchart showing an artificial neural network model training method according to an embodiment of the present disclosure.

MODE FOR INVENTION

Embodiments of the present disclosure will be described in detail below with reference to the accompanying drawings so that those having ordinary skill in the art of the present disclosure (hereinafter referred to as those skilled in the art) can easily implement the present disclosure. The embodiments presented in the present disclosure are provided to enable those skilled in the art to use or practice the content of the present disclosure. Accordingly, various modifications to embodiments of the present disclosure will be apparent to those skilled in the art. That is, the present disclosure may be implemented in various different forms and is not limited to the following embodiments.

The same or similar reference numerals denote the same or similar components throughout the specification of the present disclosure. Additionally, in order to clearly describe the present disclosure, reference numerals for parts that are not related to the description of the present disclosure may be omitted in the drawings.

The term "or" used herein is intended not to mean an exclusive "or" but to mean an inclusive "or." That is, unless otherwise specified herein or the meaning is not clear from the context, the clause "X uses A or B" should be understood to mean one of the natural inclusive substitutions. For example, unless otherwise specified herein or the meaning is not clear from the context, the clause "X uses A or B" may be interpreted as any one of a case where X uses A, a case where X uses B, and a case where X uses both A and B.

The term "and/or" used herein should be understood to refer to and include all possible combinations of one or more of listed related concepts.

The terms "include" and/or "including" used herein should be understood to mean that specific features and/or components are present. However, the terms "include" and/or "including" should be understood as not excluding the presence or addition of one or more other features, more other one or components, and/or combinations thereof.

Unless otherwise specified herein or unless the context clearly indicates a singular form, the singular form should generally be construed to include "one or more."

The term "N-th (N is a natural number)" used herein can be understood as an expression used to distinguish the components of the present disclosure according to a predetermined criterion such as a functional perspective, a structural perspective, or the convenience of description. For example, in the present disclosure, components performing different functional roles may be distinguished as a first component or a second component. However, components that are substantially the same within the technical spirit of the present disclosure but should be distinguished for the convenience of description may also be distinguished as a first component or a second component.

Meanwhile, the term "module" or "unit" used herein may be understood as a term referring to an independent functional unit processing computing resources, such as a computer-related entity, firmware, software or part thereof, hardware or part thereof, or a combination of software and hardware. In this case, the "module" or "unit" may be a unit composed of a single component, or may be a unit expressed as a combination or set of multiple components. For example, in the narrow sense, the term "module" or "unit" may refer to a hardware component or set of components of a computing device, an application program performing a specific function of software, a procedure implemented through the execution of software, a set of instructions for the execution of a program, or the like. Additionally, in the broad sense, the term "module" or "unit" may refer to a computing device itself constituting part of a system, an application running on the computing device, or the like. However, the above-described concepts are only examples, and the concept of "module" or "unit" may be defined in various manners within a range understandable to those skilled in the art based on the content of the present disclosure.

The term "model" used herein may be understood as a system implemented using mathematical concepts and language to solve a specific problem, a set of software units intended to solve a specific problem, or an abstract model for a process intended to solve a specific problem. For example, a neural network "model" may refer to an overall system implemented as a neural network that is provided with problem-solving capabilities through training. In this case, the neural network may be provided with problem-solving capabilities by optimizing parameters connecting nodes or neurons through training. The neural network "model" may include a single neural network, or a neural network set in which multiple neural networks are combined together.

In the present specification, the 'image' may refer to multi-dimensional data composed of discrete image elements (e.g., pixels in a 2D image or voxels in a 3D image). For example, an image may include medical images acquired by medical imaging machines such as a magnetic resonance imaging (MRI) machine, a computed tomography (CT) scanner, an ultrasonic scanner, and an X-ray machine.

The term "medical image" used herein is a concept collectively referring to all forms of images encompassing medical knowledge, and may include images acquired through various modalities such as visible light cameras, IR cameras, ultrasound, X-ray, CT, MRI, and PET.

The term "medical image archiving and communication system (PACS)" used herein refers to a system that stores, processes, and transmits medical images in accordance with the Digital Imaging and Communications in Medicine (DICOM) standard. For example, the "PACS" operates in conjunction with digital medical imaging equipment, and stores medical images such as magnetic resonance imaging (MRI) images and computed tomography (CT) images in accordance with the DICOM standard. The "PACS" may transmit medical images to terminals inside and outside a hospital over a communication network. In this case, meta information such as reading results and medical records may be added to the medical images.

In the present specification, the 'object' is a target for imaging, and may include a human, an animal, or a part thereof. For example, an object may include a part (organ) of the body or a phantom. The phantom refers to a volume material having a density and an effective atomic number considerably close to those of an organism, and may include a spherical phantom having properties similar to those of the body.

A magnetic resonance image (MRI) system is a system that acquires images of tomographic areas of an object by representing the intensity of a magnetic resonance (MR) signal for a radio frequency (RF) signal generated from a magnetic field having a specific intensity in the form of contrasts between light and darkness.

The MRI system allows a main magnet to form a static magnetic field, and aligns the magnetic dipole moment direction of a specific atomic nucleus of an object, located in the static magnetic field, in the direction of the static magnetic field. A gradient magnetic field coil may generate a gradient magnetic field by applying a gradient signal to the static magnetic field, thereby inducing a different resonance frequency for each portion of the object. An RF coil may radiate a magnetic resonance signal in accordance with the resonance frequency of a portion where an image is to be acquired. Furthermore, as the gradient magnetic field is formed, the RF coil may receive magnetic resonance signals of different resonance frequencies radiated from various portions of the object. The MRI system acquires an image by applying an image reconstruction technique to the magnetic resonance signals received through this step. In addition, the MRI system may reconstruct a plurality of magnetic resonance signals into image data by performing serial or parallel signal processing on the plurality of magnetic resonance signals received by multi-channel RF coils.

The foregoing descriptions of the terms are intended to help to understand the present disclosure. Accordingly, it should be noted that unless the above-described terms are explicitly described as limiting the content of the present disclosure, they should not be interpreted as limiting the technical spirit of the present disclosure.

FIG. 1 is a block diagram of a computing device according to an embodiment of the present disclosure.

A computing device 1 according to an embodiment of the present disclosure may be a hardware device or part of a hardware device that performs the comprehensive processing and calculation of data, or may be a software-based computing environment that is connected to a communication network. For example, the computing device 1 may be a server that performs an intensive data processing function and shares resources, or may be a client that shares resources through interaction with a server. Furthermore, the computing device 1 may be a cloud system in which a plurality of servers and clients interact with each other and comprehensively process data. Since the above descriptions are only examples related to the type of computing device 1, the type of computing device 1 may be configured in various manners within a range understandable to those skilled in the art based on the content of the present disclosure.

Referring to FIG. 1, the computing device 1 according to an embodiment of the present disclosure may include a processor 2, memory 3, and a network unit 4. However, FIG. 1 shows only an example, and the computing device 1 may include other components for implementing a computing environment. Furthermore, only some of the components disclosed above may be included in the computing device 1.

The processor 2 according to an embodiment of the present disclosure may be understood as a configuration unit including hardware and/or software for performing computing operation. For example, the processor 2 may read a computer program and perform data processing for machine learning. The processor 2 may process computational processes such as the processing of input data for machine learning, the extraction of features for machine learning, and the calculation of errors based on backpropagation. The processor 2 for performing such data processing may include a central processing unit (CPU), a general purpose graphics processing unit (GPGPU), a tensor processing unit (TPU), an application specific integrated circuit (ASIC), or a field programmable gate array (FPGA). Since the types of processor 2 described above are only examples, the type of processor 2 may be configured in various manners within a range understandable to those skilled in the art based on the content of the present disclosure.

According to an embodiment of the present disclosure, a processor 2 may generate training data that is input to an artificial neural network model. The artificial neural network model is trained using training data, and may output a low-quality image as a high-quality image. For example, the artificial neural network model may generate a high-quality image by removing noise from an input low-quality image.

The artificial neural network model may include at least one neural network. The neural network may include network models such as a Deep Neural Network (DNN), a Recurrent Neural Network (RNN), a Bidirectional Recurrent Deep Neural Network (BRDNN), a Multilayer Perceptron (MLP), and a Convolutional Neural Network (CNN), but is not limited thereto.

The image may be a medical image, e.g., a magnetic resonance image. In this case, the magnetic resonance image may be acquired through accelerated imaging. The accelerated imaging may be understood as imaging techniques that shortens imaging time by increasing the acceleration factor compared to regular imaging. The acceleration factor is a term used in a parallel imaging technique, and may be understood as a value obtained by dividing the number of signal lines fully sampled in the k-space domain by the number of signal lines sampled through imaging.

The processor 2 may generate k-space data and a magnetic resonance image by processing signals, i.e., magnetic resonance signals, obtained from a plurality of coils. In the present specification, k-space data and magnetic resonance images generated based on the signals received from coils are referred to as coil images.

The processor 2 may group a plurality of coil images into a plurality of groups and, for each of the plurality of groups, generate a group image by combining the coil images included in each group. In this case, the number of groups and the number of coil images belonging to each of the groups may vary depending on the channels or number of coils. For example, the processor 2 may receive signals from 16 coils, respectively, and generate 16 coil images in a 16-channel coil system. In this case, a first group and a second group may be generated to each include 8 coil images, the 8 coil images of the first group may be combined to generate a first group image, and the 8 coil images of the second group may be combined to generate a second group image.

In this case, the plurality of group images generated by combining the coil images have the same signals and are noise-independent of each other. Accordingly, the processor 2 may generate training data for an artificial neural network model for removing noise by using a plurality of group images.

In the present specification, 'grouping' may mean generating a group including a plurality of coil images. 'Grouping' may mean classifying a plurality of coil images by matching them to tags. That is, a group generated as a result of grouping includes at least one coil image.

In the present specification, 'combine' may mean generating one image by merging a plurality of coil images. 'Combine' may mean performing an operation using information included in a plurality of coil images and generating one image as a result of the operation.

Meanwhile, the sensitivity characteristics of a coil represent the differences that occur because the location of each coil is different with respect to the location of an object. In general, as the object becomes closer to the coil, the sensitivity increases, and as an object becomes further away from the coil, the sensitivity decreases. This difference in sensitivity for each coil, i.e., the sensitivity characteristics of the coil, may be represented in various manners. For example, each pixel value in a sensitivity map may represent the sensitivity of the coil at that location.

The processor 2 may group a plurality of coil images by taking into consideration the sensitivity characteristics of coils. For example, grouping may be performed such that the sensitivity characteristics of the first group image of the first group and the sensitivity characteristics of the second group image of the second group are the same.

Furthermore, the processor 2 may combine a plurality of coil images by taking into consideration sensitivity the characteristics of coils. When coils having different sensitivity characteristics are combined with each other, the differences in the brightness of a group image generated as a result of the combination may occur. Accordingly, the processor 2 may uniformly adjust the brightness of the group image by performing combination through the application of a coefficient that reflects the sensitivity characteristics therein.

As a result, according to an embodiment of the present disclosure, high-quality training data having uniform image characteristics may be generated in a multi-channel coil system. Furthermore, both input and label images may be generated using medical images acquired through a single imaging, so that the time and cost required for preparing training data for an artificial neural network model can be reduced.

According to an embodiment of the present disclosure, the processor 2 may train the artificial neural network model to improve image quality. The image may be, for example, a magnetic resonance image, or may be acquired by accelerated imaging. The accelerated imaging may be understood as an imaging technique that shortens imaging time by increasing the acceleration factor compared to regular imaging. The acceleration factor is a term used in a parallel imaging technique, and may be understood as a value obtained by dividing the number of signal lines fully sampled in the K-space domain by the number of signal lines sampled through imaging. For example, an acceleration factor of 2 can be understood as obtaining a number of signal lines equivalent to half of the number of fully sampled signal lines when lines are obtained by sampling a magnetic resonance signal in the phase encoding direction. Accordingly, as the acceleration factor increases, the imaging time of a magnetic resonance image may decrease proportionally. That is, when the acceleration factor is increased during the imaging of a magnetic resonance image, accelerated imaging in which magnetic resonance image imaging time is shortened may be implemented.

When necessary, the processor 2 may generate a user interface that provides an environment for interaction with the user of the computing device 1 or the user of any client. For example, the processor 2 may generate a user interface that receives the number of groups, criteria for grouping coil images, a method for combining coil images, and the like.

The processor 2 may generate a user interface that allows functions such as the output, modification, change, and/or addition of data to be implemented based on an external input signal applied from a user. Since the role of the user interface described above is merely an example, the role of the user interface may be defined in various manners within a range understandable to those skilled in the art based on the content of the present disclosure.

The memory 3 according to an embodiment of the present disclosure may be understood as a configuration unit including hardware and/or software for storing and managing data that is processed in the computing device 1. That is, the memory 3 may store any type of data generated or determined by the processor 2 and any type of data received by the network unit 4. For example, the memory 3 may include at least one type of storage medium of a flash memory type, hard disk type, multimedia card micro type, and card type memory, random access memory (RAM), static random access memory (SRAM), read-only memory (ROM), electrically erasable programmable read-only memory (EEPROM), programmable read-only memory (PROM), magnetic memory, a magnetic disk, and an optical disk. Furthermore, the memory 3 may include a database system that controls and manages data in a predetermined system. Since the types of memory 3 described above are only examples, the type of memory 3 may be configured in various manners within a range understandable to those skilled in the art based on the content of the present disclosure.

The memory 3 may structure, organize, and manage data required for the processor 2 to perform operations, the combination of data, and program code executable on the processor 2. For example, the memory 3 may store one or more coil images received through the network unit 4, which will be described later. Furthermore, the memory 3 may store input and label images generated from one or more coil images by the processor 2. Furthermore, the memory 3 may store program code that operates the processor 2 to generate a group image based on the coil images and to generate input and label images based on group images.

The network unit 4 according to an embodiment of the present disclosure may be understood as a configuration unit that transmits and receives data through any type of known wired/wireless communication system. For example, the network unit 4 may perform data transmission and reception using a wired/wireless communication system such as a local area network (LAN), a wideband code division multiple access (WCDMA) network, a long term evolution (LTE) network, the wireless broadband Internet (WiBro), a 5th generation mobile communication (5G) network, a ultra wide-band wireless communication network, a ZigBee network, a radio frequency (RF) communication network, a wireless LAN, a wireless fidelity network, a near field communication (NFC) network, or a Bluetooth network. Since the above-described communication systems are only examples, the wired/wireless communication system for the data transmission and reception of the network unit 4 may be applied in various manners other than the above-described examples.

The network unit 4 may receive data required for the processor 2 to perform operations through wired or wireless communication with any system or client. Furthermore, the network unit 4 may transmit data generated through the operation of the processor 2 through wired or wireless communication with any system or any client. For example, the network unit 4 may receive medical images through communication with a PACS, a cloud server for performing tasks such as the improvement of the resolution of medical images and the standardization of medical images, or the computing device 1. The network unit 4 may transmit improved images output from an artificial intelligence model and a mathematical model through communication with the above-described system, server, or computing device 1. For example, the network unit 4 may receive magnetic resonance signals generated in the respective coils from the coil system.

When necessary, the network unit 4 may provide the user interface, generated by the processor 2, to any system or client through wired or wireless communication with the system or client. For example, the network unit 4 may provide a user interface for visualizing data, processed by the processor 2, through communication with a PACS or the computing device 1 including a display to the system or device. The network unit 4 may receive an external input signal, applied from a user, through a user interface from the above-described system or device, and transmit it to the processor 2. In this case, the processor 2 may operate to implement functions such as the output, modification, change, or addition of data based on the external input signal transmitted from the network unit 4. Meanwhile, even without communication through the network unit 4, the system or device provided with a user interface may operate on its own to implement functions such as the output, modification, change, or addition of data according to an external input signal applied from the user.

FIG. 2 is an exemplary diagram showing the arrangement of coils of a multi-channel coil system according to an embodiment of the present disclosure, and FIGS. 3 and 4 are diagrams illustrating a method of operating a data processing device according to an embodiment of the present disclosure.

Referring to FIG. 2, the multi-channel coil system 10 may include a plurality of coils to be disposed around an object. Each of the coils may be an RF coil, and may radiate RF signals to the patient and receive magnetic resonance signals emitted from a patient. Each of the coils may communicate with an external device in a wired and/or wireless manner and transmit a magnetic resonance signal to an external device, e.g., the data processing device 20. The coil system 10 may include coils of various channels, such as 16 channels, 32 channels, 72 channels, and 144 channels. Although the coil system 10 including 12 channels, i.e., first to twelfth coils 111 to 122, is illustrated in FIGS. 2 and 3, the number of channels is not limited thereto.

Referring to FIG. 3, the data processing device 20 may generate coil images based on the signals generated from the first to twelfth coils 111 to 122, respectively. First to twelfth coil images 211 to 222 correspond to the first to twelfth coils 111 to 122, respectively. The first to twelfth coil images 211 to 222 may be generated based on signals obtained by imaging the object once, for example, through accelerated imaging.

The data processing device 20 may group the first to twelfth coil images 211 to 222 into two or more groups. For example, when the first to twelfth coil images 211 to 222 are grouped into two groups, the first to sixth coil images 211 to 216 may be determined to be a first group and the seventh to twelfth coil images 217 to 222 may be determined to be a second group. A method by which the data processing device 20 groups coil images will be described in detail later with reference to FIG. 5.

The coil images of the first group may be combined to generate a first group image 310, and the coil images of the second group may be combined to generate a second group image 320. As an example of a method by which the data processing device 20 performs combination, the square root of a sum may be taken after summing up the squares of the plurality of coil images included in each group. As another example, coefficients set for each coil and for each pixel of the coil image may be applied to the individual pixels of the plurality of coil images and summed up.

In the combination process, the data processing device 20 may perform a processing operation so that the sensitivity characteristics of the first group image 310 and the second group image 320 are uniform. For example, the characteristics of the first group and the sensitivity characteristics of the second group may be reflected in the coefficients set for each coil and for each pixel of the coil image. Details about this will be described later with reference to FIG. 5.

The generated first group image 310 and second group image 320 have the same signal strength and are noise-independent of each other. Accordingly, the first group image 310 and the second group image 320 may be used as training data for the artificial neural network model 500 that reduces noise in an input image.

Referring to FIG. 4, the data processing device 20 may generate the input image 410 and label image 420 of training data by using the first group image 310 and the second group image 320, and may provide the input image 410 and the label image 420 to the artificial neural network model 500. For example, the data processing device 20 may determine one of the first group image 310 and the second group image 320 to be the input image 410 and the remaining one to be the label image 420. For example, the combination ratio of the first group image 310 and the second group image 320 may be determined according to the noise reduction target value of the artificial neural network model 500, and the input image 410 and the label image 420 may be generated according to the determined combination ratio.

Although an example having two group images is illustrated in FIG. 4, there may be three or more group images. In this case, the input image 410 and the label image 420 may be generated by combining three group images.

The artificial neural network model 500 is trained to output a high-quality image from a low-quality image by using the training data.

FIG. 5 is a flowchart showing a method of operating a data processing device according to an embodiment of the present disclosure.

Referring to FIGS. 4 and 5 together, the data processing device 20 may group a plurality of coil images, generated based on the signals received from a plurality of coils, into a plurality of groups in step S110. For example, when the data processing device 20 groups a plurality of coil images into a first group and a second group, the grouping may be performed such that the sensitivity characteristics of the first group images 310 of the first group and the sensitivity characteristics of the second group images 320 of the second group are the same.

That is, the data processing device 20 may generate grouping criteria optimized such that the sensitivity characteristics of the plurality of group images are the same. More specifically, the data processing device 20 may perform the grouping so that the standard deviation of a sensitivity map corresponding to the first group image 310 and the standard deviation of a sensitivity map corresponding to the second group image 320 are each minimized.

Alternatively, the data processing device 20 may perform the grouping so that the difference between a sensitivity map corresponding to the first group image 310 and a sensitivity map corresponding to the second group image 320 is minimized.

The data processing device 20 may generate a group image for each of the plurality of groups by combining coil images included in each group in step S120. In this case, the signal strengths of the plurality of group images are the same, and the plurality of group images are noise-independent of each other.

The data processing device 20 may perform the combination so that the sensitivity characteristics of the individual group images are the same. More specifically, the data processing device 20 applies adaptive combination to the coil images included in each group. The adaptive combination method means applying the coefficients set for each coil and for each pixel of the coil image to the individual pixels of a plurality of coil images and summing up resulting values. The data processing device 20 generates a group image by adaptively combining a plurality of coil images using a sensitivity adjustment coefficient determined based on the sensitivity of coils corresponding to each group.

When the example of step S110 is applied, the data processing device 20 may determine a first sensitivity adjustment coefficient so that it is applied to the pixels of first locations for the coil images of the first group. The first sensitivity adjustment coefficient reflects the sensitivity characteristics of coils corresponding to the coil images of the first group therein. Furthermore, the data processing device 20 may determine a second sensitivity adjustment coefficient so that it is applied to the pixels of first locations for the coil images of the second group. The second sensitivity adjustment coefficient reflects the sensitivity characteristics of coils corresponding to the coil images of the second group therein. Sensitivity adjustment coefficients re determined for all the pixels of each coil image and the sensitivity adjustment coefficient are applied, so that the coil images can be combined to generate a group image.

The data processing device 20 may generate the input image 410 and the label image 420 that are input to the artificial neural network model 500 that outputs a high-quality medical image based on a low-quality medical image by combining a plurality of group images in step S130.

FIGS. 6 and 7 are diagrams illustrating the combination operation of a data processing device according to an embodiment of the present disclosure.

Referring to FIGS. 3, 4, 6 and 7 together, the data processing device 20 may determine sensitivity adjustment coefficients that reflect the sensitivity characteristics of coils corresponding to each group and the pixel location of each coil image therein, and may combine coil images based on the sensitivity adjustment coefficients.

Assuming that all the first to twelfth coil images 211 to 222 are combined, the data processing device 20 may determine different coefficients for the respective first to twelfth coil images 211 to 222 depending on the sensitivity characteristics of the first to twelfth coils 111 to 122 for a first pixel at location (1,1).

The coefficient applied to the first pixel of the first coil image 211 is a1 (1,1), and the coefficient applied to the first pixel of the twelfth coil image 222 is a12 (1,1). In this case, the sum of squares of the respective coefficients may be normalized to be 1. That is, this may be represented by Equation 1:

$$\sum\nolimits_{n=1}^{12} a_n(1,1) = 1 \tag{1}$$

where n denotes the number of the coil, and a denotes the coefficient.

In this case, the first to sixth coil images 211 to 216 may be grouped into the first group, and the seventh to twelfth coil images 217 to 222 may be grouped into the second group. In this case, the sums of squares of respective coefficients for the first pixels of the first and second groups may be represented by Equation 2:

$$\sum\nolimits_{n=1}^{6} a_n(1,1) = \frac{3}{4},\ \sum\nolimits_{n=7}^{12} a_n(1,1) = \frac{1}{4} \tag{2}$$

This indicates that the sensitivity of the first to sixth coils 111 to 116 is lower than the sensitivity of the seventh to twelfth coils 117 to 122 and needs to be multiplied by a larger weight.

That is, when the sensitivity of coils corresponding to the first group is smaller than the sensitivity of coils corresponding to the second group, the sensitivity adjustment coefficient of the first group may be larger than the sensitivity adjustment coefficient of the second group.

When adaptive combination is applied to the first to sixth coil images 211 to 216 of the first group, the data processing device 20 may reflect the sum of squares of respective coefficients, calculated when all the coil images are adaptively combined, as a sensitivity adjustment coefficient. For example, when the value of the first pixel of the first group image 310 is determined by combining the first pixels of the first to sixth coil images 211 to 216, it can be multiplied by ¾, which is a sensitivity adjustment coefficient. Furthermore, when the value of the first pixel of the second group image 320 is determined by combining the first pixels of the seventh to twelfth coil images 217 to 222, it may be multiplied by ¼, which is a sensitivity adjustment coefficient.

FIG. 8 is a flowchart showing an artificial neural network model training method according to an embodiment of the present disclosure.

Referring to FIGS. 4 and 8 together, the artificial neural network model 500 may receive the input and label images 410 and 420 generated based on medical images from the data processing device 20 in step S210.

The artificial neural network model 500 may be trained to output a high-quality medical image based on a low-quality medical image by using the input and label images 410 and 420 in step S220.

The foregoing description of the present disclosure is intended for illustrative purposes, and a person having ordinary skill in the art to which the present disclosure pertains will understand that modifications into other specific forms may be easily performed without departing from the technical spirit or essential features of the present disclosure. Therefore, it should be understood that the embodiments described above are all illustrative but not restrictive in all respects. For example, each component described as single may be implemented in a distributed manner, and similarly, components described as distributed may also be implemented in a combined form.

The scope of the present disclosure is defined by the attached claims rather than the detailed description above, and all variations and/or modifications derived from the meanings and scope of the attached claims and their equivalent concepts should be construed as being included in the scope of the present disclosure.

The invention claimed is:

1. A data processing method for generating training data, the data processing method being performed by a computing device including at least one processor, the data processing method comprising:

grouping a plurality of coil images, generated based on signals received from a plurality of coils, into a plurality of groups;

for each of the plurality of groups, generating a group image by combining coil images included in each group; and generating an input image and a label image to be input to an artificial neural network model that outputs a high-quality medical image based on a low-quality medical image by combining a plurality of the group images, wherein the plurality of the group images have the same signal strength and are noise-independent of each other.

2. The data processing method of claim 1, wherein:

the plurality of groups comprise a first group and a second group; and grouping the plurality of coil images into the plurality of groups comprises grouping the plurality of coil images so that sensitivity characteristics of first group images of the first group correspond to sensitivity characteristics of second group images of the second group.

3. The data processing method of claim 2, wherein grouping the plurality of coil images into the plurality of groups comprises grouping the plurality of coil images so that a standard deviation of a sensitivity map corresponding to the first group images and a standard deviation of a sensitivity map corresponding to the second group images are each minimized.

4. The data processing method of claim 2, wherein grouping the plurality of coil images into the plurality of groups comprises grouping the plurality of coil images so that a difference between a sensitivity map corresponding to the first group images and a sensitivity map corresponding to the second group images is minimized.

5. The data processing method of claim 1, wherein generating the group image by combining the coil images included in each group comprises combining the coil images included in each group so that sensitivity characteristics of individual group images correspond to each other.

6. The data processing method of claim 5, wherein generating the group image by combining the coil images included in each group comprises generating the group image by adaptively combining the coil images included in each group by using a sensitivity adjustment coefficient determined based on sensitivity of coils corresponding to each group.

7. The data processing method of claim 6, wherein:

the plurality of groups comprise a first group and a second group; and generating the group image by combining the coil images included in each group comprises generating a first group image of the first group and a second group image of the second group based on a first sensitivity adjustment coefficient determined to be applied to pixels of first locations for coil images of the first group and a second sensitivity adjustment coefficient determined to be applied to pixels of first locations for coil images of the second group.

8. The data processing method of claim 7, wherein, with respect to the pixels of the first locations, when sensitivity of coils corresponding to the first group is higher than sensitivity of coils corresponding to the second group, the first sensitivity adjustment coefficient is smaller than the second sensitivity adjustment coefficient.

9. The data processing method of claim 1, wherein the plurality of coil images are generated based on signals obtained by imaging an object once.

10. The data processing method of claim 9, wherein the plurality of coil images are generated based on signals obtained by performing accelerated imaging on the object.

11. A data processing device for generating training data, comprising:

memory configured to store a plurality of coil images generated based on signals received from a plurality of coils; and a processor configured to;

group the plurality of coil images into a plurality of groups and, for each of the plurality of groups;

generate a group image by combining coil images included in each group; and generate an input image and a label image to be input to an artificial neural network model that outputs a high-quality medical image based on a low-quality medical image by combining a plurality of the group images, wherein the plurality of the group images have the same signal strength and are noise-independent of each other.

12. The data processing device of claim 11, wherein the processor is configured to combine the coil images included in each group based on sensitivity characteristics of coils corresponding to each group and a sensitivity adjustment coefficient reflecting pixel locations of each coil image therein.

13. The data processing device of claim 12, wherein the processor is configured to:
- group the plurality of coil images into a first group and a second group; and
- with respect to pixels of first locations for the individual coil images, when sensitivity of coils corresponding to the first group is higher than sensitivity of coils corresponding to the second group, combine the coil images by applying a sensitivity adjustment coefficient smaller than a sensitivity adjustment coefficient of coil images of the second group to coil images of the first group.

14. A non-transitory computer-readable storage medium having instructions stored thereon that, when executed by at least one processor, cause the at least one processor to generate training data by performing a method comprising operations of:
- grouping a plurality of coil images, generated based on signals received from a plurality of coils, into a plurality of groups;
- for each of the plurality of groups, generating a group image by combining coil images included in each group; and
- generating an input image and a label image to be input to an artificial neural network model that outputs a high-quality medical image based on a low-quality medical image by combining a plurality of the group images,
- wherein the plurality of the group images have the same signal strength and are noise-independent of each other.

* * * * *